(12) United States Patent
Doskocil et al.

(10) Patent No.: US 11,786,722 B2
(45) Date of Patent: Oct. 17, 2023

(54) SELECTIVE NEUROMODULATION APPARATUS

(71) Applicant: TESLA MEDICAL S.R.O., Ostrava (CZ)

(72) Inventors: Lukas Doskocil, Choceň (CZ); Zdenek Krcil, Pardubice (CZ)

(73) Assignee: STIMVIA s.r.o., Ostrava-Pustkovec (CZ)

( * ) Notice: Subject to any disclaimer, the term of this patent is extended or adjusted under 35 U.S.C. 154(b) by 0 days.

(21) Appl. No.: 17/364,262

(22) Filed: Jun. 30, 2021

(65) Prior Publication Data

US 2022/0001165 A1   Jan. 6, 2022

Related U.S. Application Data

(60) Provisional application No. 63/047,642, filed on Jul. 2, 2020.

(51) Int. Cl.
*A61N 1/04* (2006.01)
*A61N 1/08* (2006.01)
*A61N 1/36* (2006.01)

(52) U.S. Cl.
CPC ......... *A61N 1/0456* (2013.01); *A61N 1/0476* (2013.01); *A61N 1/08* (2013.01);
(Continued)

(58) Field of Classification Search
CPC ............... A61N 1/0456; A61N 1/0476; A61N 1/36031; A61N 1/08; A61N 1/0484; A61N 1/0492
See application file for complete search history.

(56) References Cited

U.S. PATENT DOCUMENTS 5,775,331 A * 7/1998 Raymond ............... A61B 5/05
600/554
8,108,049 B2 * 1/2012 King .................. A61N 1/36185
607/117

(Continued)

FOREIGN PATENT DOCUMENTS

| WO | 2008075250 A1 | 6/2008 |
| WO | 2009138961 A1 | 11/2009 |
| WO | 2020006607 A1 | 1/2020 |

OTHER PUBLICATIONS

International Search Report related to PCT/EP2021/062354; dated Jul. 23, 2021.

(Continued)

*Primary Examiner* — Alyssa M Alter
(74) *Attorney, Agent, or Firm* — von Briesen & Roper, s.c.

(57) ABSTRACT

A neuromodulation apparatus and method of using the same. The neuromodulation apparatus has a plurality of active electrodes electrically isolated from each other and arranged in at least one electrodes array, at least one reference electrode, a pulse generator electrically connected to each active electrode of the plurality of active electrodes and configured to selectively transmit electric pulses to each of the plurality of active electrodes and a control unit coupled to the electrical pulse generator and adapted to measure a resistance and/or a current-voltage characteristic between each active electrode of the plurality of active electrodes and the at least one reference electrode.

19 Claims, 6 Drawing Sheets

(52) U.S. Cl.
CPC ..... *A61N 1/36007* (2013.01); *A61N 1/36021* (2013.01); *A61N 1/36025* (2013.01); *A61N 1/36031* (2017.08)

(56) References Cited

U.S. PATENT DOCUMENTS

| | | | |
|---|---|---|---|
| 2006/0085049 A1* | 4/2006 | Cory | A61B 5/4041 607/48 |
| 2018/0185630 A1* | 7/2018 | Fenton | A61N 1/36007 |
| 2020/0069941 A1 | 3/2020 | Campean et al. | |

OTHER PUBLICATIONS

Malesevic et al.; "A multi-pad electrode based functional electrical stimulation system for restoration of grasp"; Journal of NeuroEngineering and Rehabilitation, Sep. 2012; pp. 1-12.

Extended European Search Report related to Application No. 20183816.6; dated Dec. 9, 2020.

* cited by examiner

SELECTIVE NEUROMODULATION APPARATUS

CROSS REFERENCE TO RELATED APPLICATION

This Application claims priority under 35 U.S. § 119(e) to U.S. Provisional Patent Application No. 63/047,642 filed on Jul. 2, 2020.

FIELD OF THE DISCLOSURE

The present disclosure generally relates to a selective and effective neuromodulation. More particularly, the disclosure relates to a neuromodulation apparatus enabling an accurate targeting of a neuromodulation signal from a signal generator onto the target nerve.

BACKGROUND OF THE DISCLOSURE

This section provides background information related to the present disclosure which is not necessarily prior art.

Electrical neuromodulation has been used for a treatment of pain, urinary incontinence, mental and other difficulties, as well as for the prevention of vascular disease.

Traditional systems utilize a simple neuromodulation electrodes in the form of a body invasive needle electrodes inserted into the immediate vicinity of the nerve to be stimulated. The need of insertion of the needle electrodes into the immediate vicinity of the nerve is always associated with a risk of an incorrect placement of the electrode and consequent nerve damage or a lower than desired efficiency of the neuromodulation when not placed into the immediate vicinity of the target nerve.

In recent years became known a new non-invasive method utilizing electrodes made of metal enabling a modulation of a desired nerve. Such electrodes would be placed with their respective ends onto a stimulation point on a patient's skin. The stimulation point is typically determined as being in a proximate expected position based on an experience and human body knowledge. The setting of the intensity of neuromodulation pulses is typically factory pre-set.

Such approach bears a disadvantage of missing the most advantageous neuromodulation position for the electrodes having a significant impact on whole neuromodulation treatment as the therapeutic efficacy of neuromodulation is attributed to selective activation of targeted tissue or neural circuitry. Additionally, the electrodes may move during neuromodulation further deter therapeutic benefit.

Therefore, it would be advantageous to have an apparatus that takes into account at least some of the issues discussed above as well as possibly other issues.

SUMMARY OF THE DISCLOSURE

One objective of the present disclosure is to remedy at least part of these drawbacks. An aspect of the present disclosure is directed to a neuromodulation apparatus. The neuromodulation apparatus comprises a plurality of active electrodes electrically isolated from each other and arranged in at least one electrodes array. Each active electrode comprises an electrically conductive element applicable to or under a skin of a patient. The neuromodulation apparatus further comprises at least one reference electrode applicable to or under the skin of the patient, a pulse generator electrically connected to each active electrode of the plurality of active electrodes and configured to selectively transmit electric pulses to each of the plurality of active electrodes, a control unit coupled to the electrical pulse generator and adapted to measure a resistance and/or a current-voltage characteristic between each active electrode of the plurality of active electrodes and the at least one reference electrode. Based on the measured resistance and/or current-voltage characteristic the control unit is adapted to both control a shape of the electrical pulses and select which an active electrode or active electrodes of the plurality of active electrodes are to receive the electrical pulses generated by the pulse generator.

In another aspect, the control unit is configured to repeatably measure the resistance and/or the current-voltage characteristic between each active electrode of the plurality of active electrodes and the at least one reference electrode.

In another aspect, based on the repeatable measurement the control unit is further configured to update the selection of which of an active electrode or active electrodes of the plurality of active electrodes are to receive the electrical pulses generated by the pulse generator.

In another aspect, the neuromodulation apparatus further comprising at least one detector configured to detect a response of the patient to at least one pulse generated by the pulse generator. The detector is further adapted to provide feedback on the detected response to the control unit.

In another aspect, the at least one detector is at least one motion detector configured to detect a movement of the patient and adapted to provide feedback on the movement to the control unit, wherein the movement of the patient body is in response to the at least one pulse of the pulse generator.

In another aspect, the at least one motion detector includes at least one of an accelerometer, an electrical field sensor or a camera.

In another aspect, the control unit is further adapted to individually select each of the active electrodes of the plurality of electrodes for a reception of at least one pulse generated by the pulse generator and the control unit is further adapted to receive a patient's response detected by the detector to the at least one pulse generated by the pulse generator for each of the individually selected active electrodes of the plurality of electrodes.

In another aspect, the control unit is adapted to both control a shape of the electrical pulses and select which active electrodes of the plurality of active electrodes are to receive the electrical pulses generated by the pulse generator based on the measured resistance and/or current-voltage characteristic and the detected response by the at least one detector.

In another aspect, the control unit is further configured to determine current density of electrical pulses flowing through each of selected active electrodes and based on the result selectively employ active electrodes neighboring to the each of the selected active electrodes within the same electrodes array to also receive electrical pulses generated by the pulse generator.

In another aspect, the control unit is configured to control a slope of rising edge of the electric pulses and/or a magnitude of the electric pulses.

In another aspect, wherein the control unit is further configured to control a pulse period and/or a pulse width of the electric pulses.

In another aspect, the neuromodulation apparatus further including a probe having a contact surface which bears the electrode array, the contact surface comprising a bump which has at least part of the active electrodes of the electrode array.

In another aspect, the electrode array extends on the contact surface around the bump.

In another aspect, the contact surface has in first direction a general concave shape from which the bumps protrudes, wherein the contact surface has in second direction that is perpendicular to the first direction a general convex shape.

A further aspect is directed to a method of using the neuromodulation apparatus comprising: applying a plurality of active electrodes arranged in at least one electrodes array to a skin of a patient in a probable location of a target nerve to be stimulated or modulated, wherein the active electrodes are electrically isolated from each other, applying at least one reference electrode to the skin of the patient, measuring by a control unit a resistance and/or a current-voltage characteristic between each active electrode of the plurality of active electrodes and the at least one reference electrode, selecting based on the measured values by the control unit an active electrode or active electrodes of the plurality of active electrodes for receiving an electrical pulse generated by a pulse generator electrically selectively connected to each active electrode of the plurality of active electrodes, and controlling by the control unit a shape of the electrical pulses generated by the pulse generator based on the measured value.

In a further aspect, the method includes repeatably measuring the resistance and/or the current-voltage characteristic between each of active electrodes arranged within each of the at least one electrodes array and each of the at least one reference electrode and updating the measured values with the new measurements for each of the at least one electrode array.

In a further aspect, the method includes detecting a response of the patient's body to the at least one pulse generated by the pulse generator and providing feedback on the detected response to the control unit.

In a further aspect, the method includes applying at least one pulse generated by the pulse generator to each individual active electrodes of the plurality of electrodes and receiving a patient's response detected by the detector for each active electrode of the plurality of electrodes.

In a further aspect, the selecting the active electrodes for receiving an electrical pulse generated by a pulse generator is also based on the patient's response detected by the detector for each individual active electrode of the plurality of electrodes.

In a further aspect, the method includes determining current density of electrical pulses flowing through each of selected active electrodes and based on the result selectively employing active electrodes neighboring to the each of the selected active electrodes within the same electrodes array to also receive electrical pulses generated by the pulse generator.

A further aspect is directed to a method of using the neuromodulation apparatus as defined above or any commercially available neuromodulation apparatus for a medical treatment of at least one of overactive bladder, migraine, erectile dysfunction, spermatogenesis disorders, infertility, premature ejaculation or a bbenign prostatic hyperplasia.

In a further aspect, the method for the medical treatment includes: applying plurality of active electrodes arranged in at least one electrodes array to a skin of a patient, wherein the at least one electrodes array is positioned in the probable location of at least one of sciatic, pudendal, peroneal, cavernous, sacral plexus, vagus or a tibial nerve.

In a further aspect, the method for the medical treatment includes: applying the at least one electrodes array in the probable location of a lumbosacral plexus, common peroneal, superior gluteal, inferior gluteal, posterior cutaneous femoral, obturator internus, piriformis, quadratus femoris, plantar, vagus or coccygeal nerve.

In a further aspect, the method for the medical treatment includes: applying plurality of active electrodes arranged in at least one electrodes array to a skin of a patient, wherein the at least one electrodes array is positioned in the probable location of at least one of nerves contains sensorics and motoric fibers. Accurate position of active electrode or active electrodes of the plurality of electrodes may be confirmed by a detected response of the patient to the at least one electric pulse generated by the pulse generator. The response may involve a motion response of the patient's leg such as the inflexion of the toe or a movement of tip of the foot.

In a further aspect, the method for the medical treatment includes: applying plurality of active electrodes arranged in at least one electrodes array to a skin of a patient, wherein the at least one electrodes array is positioned in the location of common peroneal nerve (back of the knee). Accurate position of active electrode may be confirmed by detected response of the patient to the at least one electric pulse generated by the pulse generator. Accurate position of active electrode or active electrodes of the plurality of electrodes may be confirmed by a detected response of the patient to the at least one electric pulse generated by the pulse generator. The response may involve a motion response of the patient's leg such as the inflexion of the toe or a movement of a tip of the foot.

In a further aspect, the method for the medical treatment includes: applying plurality of active electrodes arranged in at least one electrodes array to a skin of a patient, wherein the at least one electrodes array is positioned in the location of tibial nerve that may be in the back of the knee or behind of the medial malleolus. Accurate position of active electrode or active electrodes of the plurality of electrodes may be confirmed by a detected response of the patient to the at least one electric pulse generated by the pulse generator. The response may involve a motion response of the patient's leg such as the inflexion of the toe or a movement of the tip of the foot.

In a further aspect, the method for the medical treatment can be used in conjunction with, or as a part of, the method of using a neuromodulation apparatus as defined above.

Further areas of applicability will become apparent from the description herein. The description and specific examples in the summary are intended for purposes of illustration only and are not intended to limit the scope of the present disclosure.

BRIEF DESCRIPTION OF THE DRAWINGS

Other features and advantages of the invention appear from the following detailed description of some of its embodiments, given by way of non-limiting example, and with reference to the accompanying drawings, in which.

DETAILED DESCRIPTION

Figure 1:
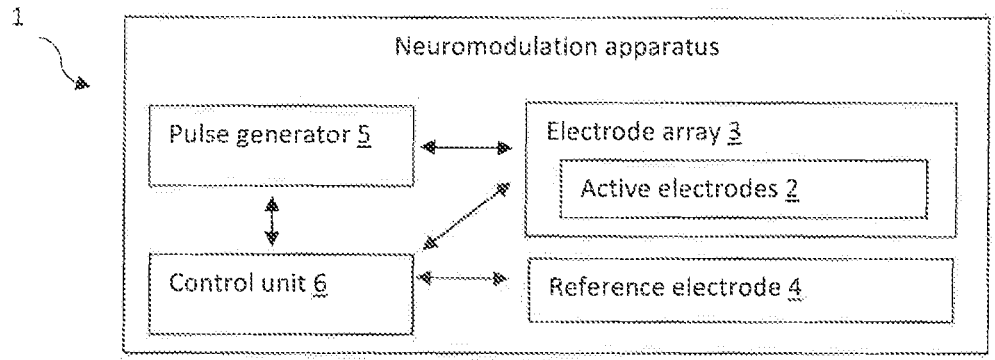
FIG. 1 is a block diagram depicting an embodiment of a neuromodulation apparatus.

The foregoing summary, as well as the following detailed description of certain examples will be better understood when read in conjunction with the appended drawings. As used herein, an element or step recited in the singular and proceeded with the word "a" or "an" should be understood as not excluding plural of the elements or steps, unless such exclusion is explicitly stated. Further, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

In the figures, the same references denote identical or similar elements, unless stated otherwise. In the drawings, the size of each element or a specific portion constituting the element is exaggerated, omitted, or schematically shown for convenience and clarity of description. Thus, the size of each component may not entirely reflect the actual size. In the case where it is judged that the detailed description of the related known functions or constructions may unnecessarily obscure the gist of the present disclosure, such explanation will be omitted.

In FIG. 1 is depicted a block diagram of an exemplary embodiment of a neuromodulation apparatus 1. The embodiment comprises plurality of active electrodes 2 arranged in an electrode array 3, a reference electrode 4, a pulse generator 3 and a control unit 4. The pulse generator 5 may be electrically connected to each electrode of the plurality of active electrodes 2 and the pulse generator may be also electrically connected to the reference electrode. The neuromodulation apparatus may have plurality of electrode arrays and/or plurality of reference electrodes.

The pulse generator 5 may selectively transmit electric pulses individually to each of the plurality of active electrodes 2 or the pulse generator 5 may selectively transmit electrical pulses to several active electrodes of the plurality of active electrodes. The electrode array 3 may be applicable to a skin of a patient. Each of the active electrode of the plurality of active electrodes 2 arranged in the electrode array may have an electrically conductive element that may be applicable to and/or under a skin of a patient. The reference electrode 4 may be also applicable to and/or under the skin of the patient and the reference electrode 4 may also include a conductive element applicable to or under the skin of the patient. Provided the plurality of active electrodes and the reference electrode are both applied to a skin of the patient then a resistance 7 and/or a current-voltage characteristic 8 between each active electrode of the plurality of active electrodes 2 and the reference electrode 4 may be measured.

Figure 2:
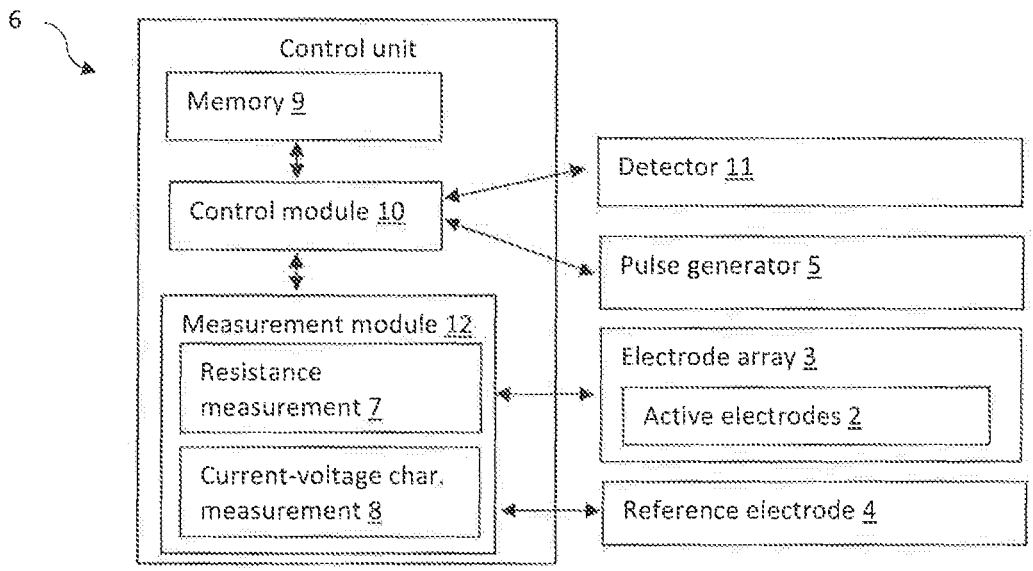
FIG. 2 is a block diagram depicting an embodiment of a control unit.

As depicted in FIG. 2 an embodiment of a control unit 6 may be coupled to the pulse generator 5 and may measure a resistance 7 and/or a current-voltage characteristic 8 between each active electrode of the plurality of active electrodes 2 and a reference electrode 4. The plurality of active electrodes may be arranged in one or more electrode arrays and there may be one or more reference electrodes. In such case the control unit may measure a resistance 7 and/or a current-voltage characteristic 8 between each active electrode of the plurality of active electrodes 2 and the at least one reference electrode 4. The control unit 6 may comprise a control module 10 and a measurement module 12. The measurement module 12 may perform a resistance measurement 7 and/or current-voltage characteristic measurement 8. The control module 10 and measurement module 12 may be electrically connected so that the control module 10 can read and interpret data provided by the measurement module 12. The control module 10 may control the measurements carried out by the measurement module 12. The control module 10 of the control unit 6 may repeatably measure the resistance and/or the current voltage characteristic. The control module 10 of the control unit 6 may perform a periodical or an individual measurement of the resistance and/or the current-voltage characteristic. The repeatable measurement taken by the control unit 6 may be used to update the selection of which of an active electrode or active electrodes of the plurality of active electrodes 2 are to receive the electrical pulses generated by the pulse generator 5.

The control unit 4 may further comprise a memory 9. For each individual active electrode of the plurality of active electrodes, the control unit may store the resistance 7 and/or a current-voltage characteristic measured data in the memory 9. For each individual active electrode of the plurality of active electrodes, the control unit may read the stored resistance 7 and/or a current-voltage characteristic measured data from the memory 9. Based on the measured resistance and/or current voltage characteristic the control unit 6 may control shape of the electrical pulses generated by the pulse generator 5 and/or select which active electrode or active electrodes are to receive the electrical pulse generated by the pulse generator 5. In one example the control unit evaluates active electrodes arranged in the same electrode array based on their measured resistance and/or current voltage characteristic. Then the control unit may select the active electrodes with lowest measured values of resistance and/or values of current voltage characteristic for reception of electrical pulses. On benefit of such example is that the lowest measured values of resistance and/or values of current voltage characteristic indicate closest proximity to a nerve in the patient body. As there may be more nerves close to each other the evaluation of several individual active electrodes with lowest measured values enables to individually evaluate active electrodes that are closest to the nerves and based on further evaluation select the desired nerve for the neuromodulation.

The control unit 6 may employ a control module 10 to store and read the data from the memory 9. The control module 10 may store the data measured by the measurement module 12 in the memory 9. The control module 12 may further process and/or interpret the measured data before storing them. The control module 10 may store and read a patient related data to the memory 9 and may match the patient's data with the measured data and vice versa. The control module 10 may be further configured to store to the memory 9 and read from the memory 9 the neuromodulation apparatus' 1 settings data related to a specific patient. The settings data may be measurements and/or generated pulse settings. The control module 10 may further match the patient's data with the measured data and vice versa. The control module 10 may further match the neuromodulation apparatus' settings data with the patient's data and the measured data.

Figure 4:
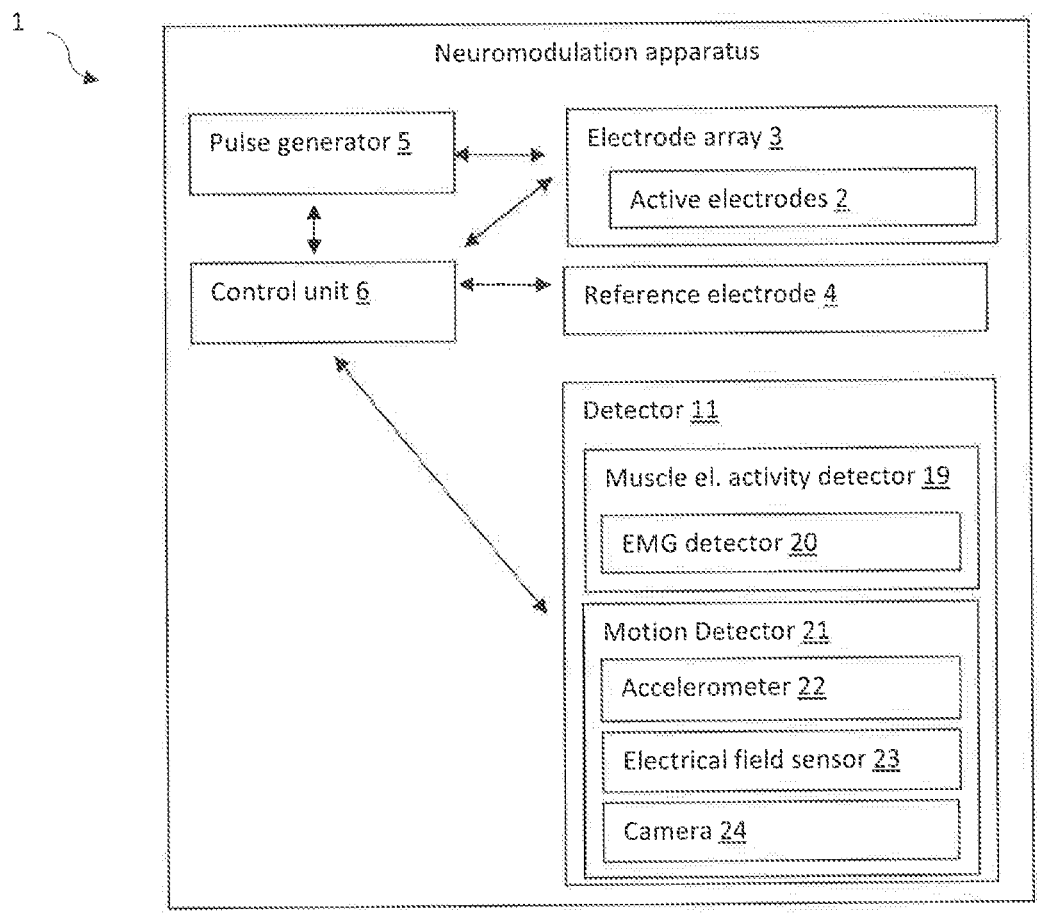
FIG. 4 is a block diagram depicting another embodiment of the neuromodulation apparatus.

The neuromodulation apparatus 1 may further comprise at least one detector 11 to detect a response of the patient to at least one pulse generated by the pulse generator 5 as shown in FIG. 4 depicting an embodiment of the neuromodulation apparatus 1. The at least one detector 11 as depicted on FIG. 2 may provide feedback on the detected response to the control unit 6. The at least one detector 11 may provide feedback to the control module 10 of the control unit 6. The at least one detector may be at least one motion detector 21 configured to detect a movement of the patient. The at least one detector may be adapted to provide feedback on the patient's movement to the control unit 6. The movement of the patient body may be in response to the at least one pulse of the pulse generator that may be conveyed via selected active electrodes attached to or under the patient's skin. The at least one motion detector 21 includes at least one of an accelerometer 22, an electrical field sensor 23 or a camera 24. Alternatively, the at least one detector 11 may be configured to detect a change in an electrical activity produced by muscles as a response to the at least one pulse generated by the pulse generator 5 and conveyed via selected active electrodes attached to or under the patient's skin. Such muscle electrical activity detector 19 may be an electromyography based (EMG) detector 20.

Figure 5:
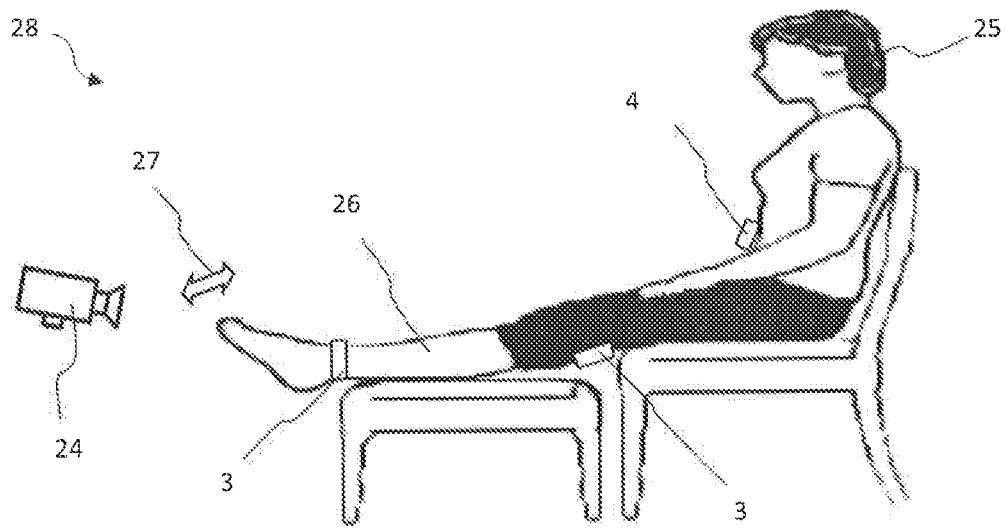
FIG. 5 is an exemplary illustration of electrodes placement on a patient with a camera as a motion detector.
Figure 6:
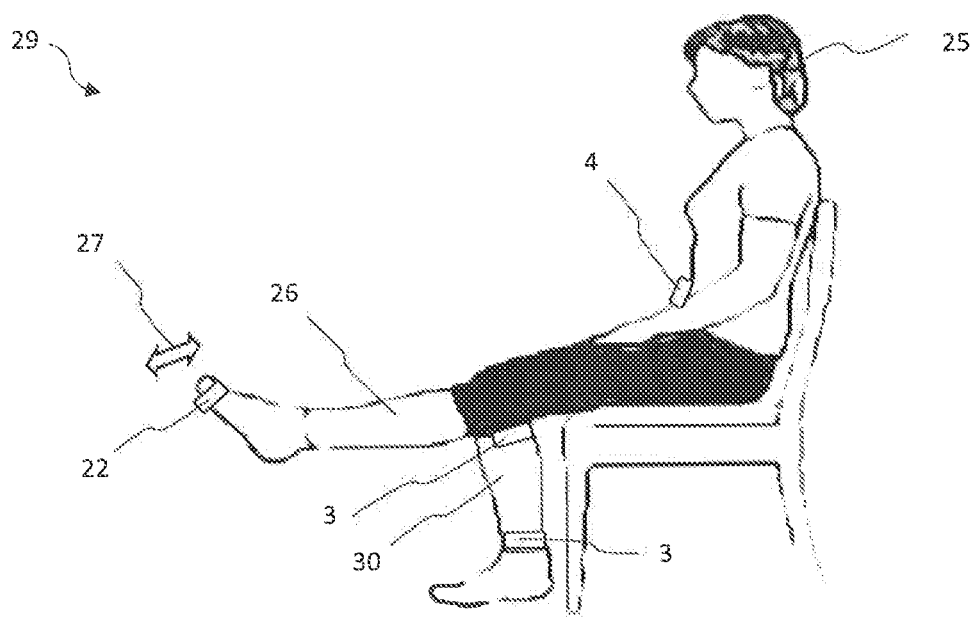
FIG. 6 is an exemplary illustration electrodes placement on a patient with an accelerometer as a motion detector.

Preferably as depicted on FIG. 6 when using the accelerometer 22 as the motion detector then the accelerometer 22 may be attached to a foot of one of the patient's legs 26, 30. Advantageously, there may be two accelerometers 22 utilized as two motion detectors each attached to different foot of the patient's legs 26, 30. Optionally, as depicted on FIG. 5 when using the camera 24 as the motion detector 21 then the camera may be located in proximity of the detected motion being oriented so to detect the motion. Optionally, an electrical field sensor 23 can be used as a motion detector 21. The electrical field sensor 23 may use an electrical field change to detect a movement of the patient. An example of such electrical field sensor may be a three-dimensional gesture recognition and tracking controller chip, which uses an electric field to provide gesture information as well as positional data of the human limb in real time. Advantageously, a combination of motion detectors selected from one or more of a camera 24, an accelerometer 22 and electrical field sensor 23 may be used. This may lead to an improvement of sensed movement accuracy and also provide redundancy of detection.

Figure 3:
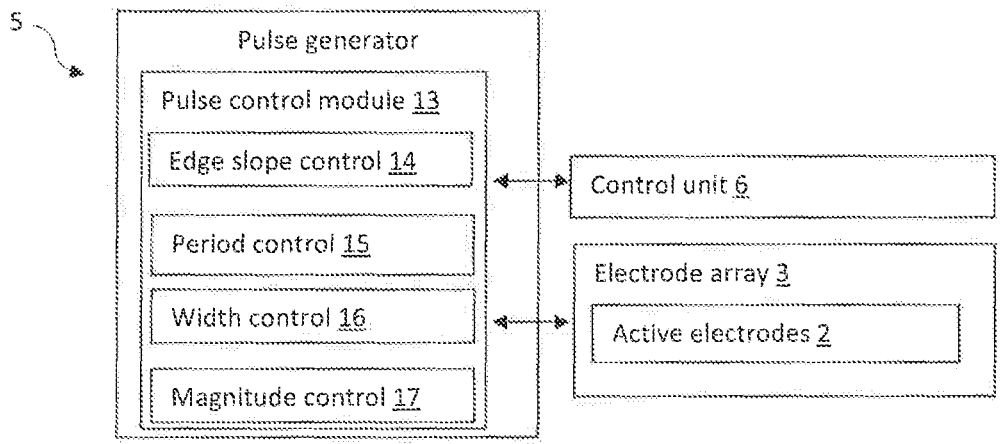
FIG. 3 is a block diagram depicting an embodiment of a pulse generator.
Figure 12:
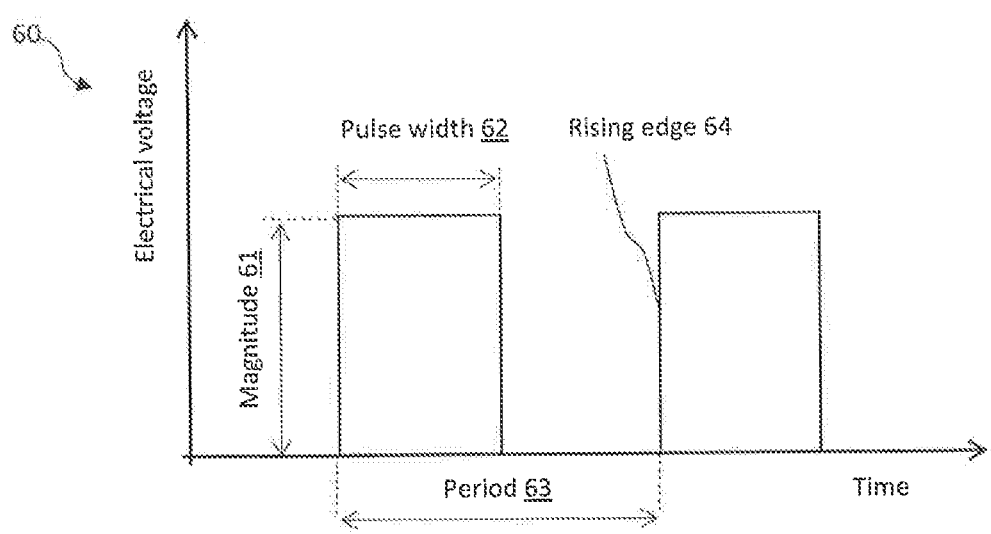
FIG. 12 is an exemplary illustration of an electrical pulse variables.

The control unit 6 may also control a shape of the electric pulses generated by the pulse generator 5 based on the measured resistance and/or current-voltage characteristic. As depicted in FIG. 3 showing an embodiment of the pulse generator 5. The pulse generator 5 may be controlled by the control unit 6 or the pulse generator may be controlled directly. Preferably, the pulse generator 5 comprises a pulse control module 13 connected with the control unit 6. The connection between the pulse control module 13 and the control unit 6 may be wired connection for instance via a cable or a wireless connection. Preferably, the pulse control module 13 is further connected with the plurality of electrodes 2 arranged in at least one electrode array 3. The connection between the pulse control module 13 and the plurality of electrodes 2 may be a wired connection for instance via a cable or a wireless connection. The pulse control module 13 may comprise an edge slope control module 14 configured to enable control the slope of an edge of a pulse generated by the pulse generator. As depicted in FIG. 12 depicting an exemplary pulse profile 60 the controlled edge may be a raising edge 64 and/or the falling edge of the pulse. The pulse control module 6 may further comprise a period control module 8 configured to enable control of a generated pulse period 63. The pulse control module 6 may further comprise a pulse width control module 9 configured to enable control of a generated pulse width 62. The pulse width control module 9 may enable pulse width modulation of the pulse. The pulse control module 6 may further comprise a magnitude control module 10 configured to enable control of a generated pulse magnitude 61.

FIGS. 5 and 6 provide exemplary illustrations 28, 29 of a placement of at least one of electrodes arrays 3 having plurality of active electrodes 2 onto or under the patient's skin 25 where at least one of the electrode arrays 3 may be applicable to a limb 26 of the patient 25 and detected movement of the patient may be a movement 27 of the limb. The at least one of the electrode arrays 3 may be applicable to an ankle to the back of the knee of the limb 26, 30. The reference electrode 4 may be applicable to an abdomen of the patient 25. Alternatively, the reference electrode 4 may be applicable elsewhere such as at a hip or a waste of the patient 25. The motion detector 21 may be a camera 24 or an electrical field sensor 23. The motion detector may detect a movement 27 of the limb 26. The movement of the limb may be in response to the at least one pulse of the pulse generator being delivered to the at least one active electrode within the electrode array 3 placed onto or under the patient's skin.

Figure 7:
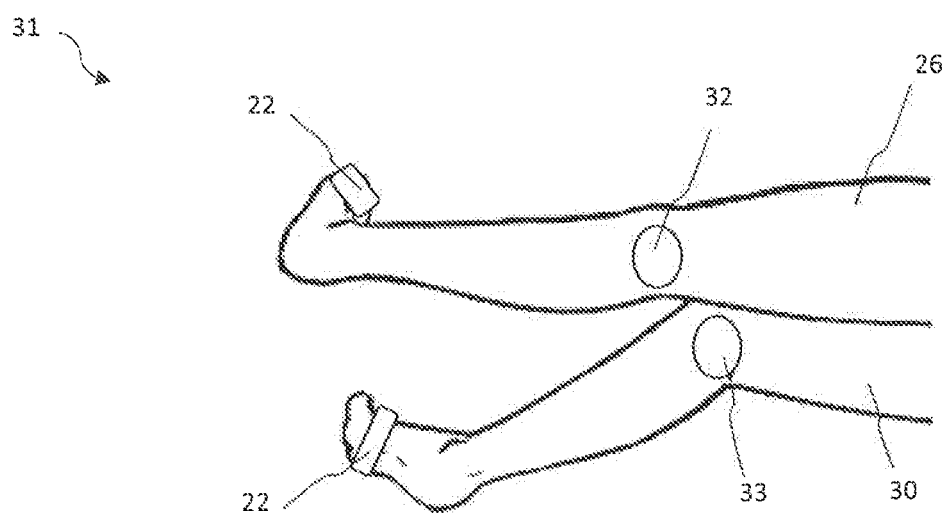
FIG. 7 is an exemplary illustration of electrodes positioning on the patient.

An advantageous embodiment 31 of electrode arrays placements on both patient legs 26 and 30 is depicted in FIG. 7. Two electrode arrays 32, 33 may be applicable to a back of the knees of a patient 25. The first electrode array 32 may be applicable to the back of a knee of a first leg 26 of the patient 25 and the second electrode array 33 may be applicable to the back of a knee of a second leg 30 of the patient 25. Alternatively, the first electrode array 32 may be applicable to a first leg 26 in proximity of the ankle of the first leg 26 of the patient 25. The second electrode array 33 may be applicable to a second leg 30 of the patient 25 in a proximity of the ankle of the second leg 30 of the patient 25. Each of the legs 26, 30 may have attached one motion detector 21 that may be an accelerometer 22. Each of the accelerometers 22 may be attached to the foot of one of the legs 26, 30. Preferably, each of the accelerometers 22 may be attached to its respective foot in the area of tip of the foot.

Figure 8:
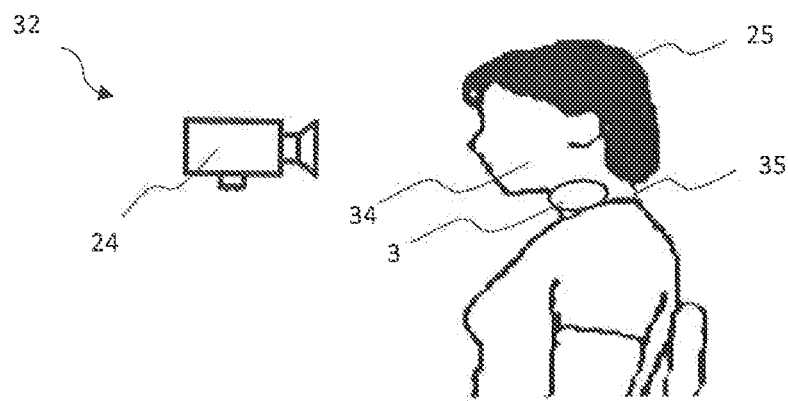
FIG. 8 is another exemplary illustration of electrodes placement on the patient.
Figure 9:
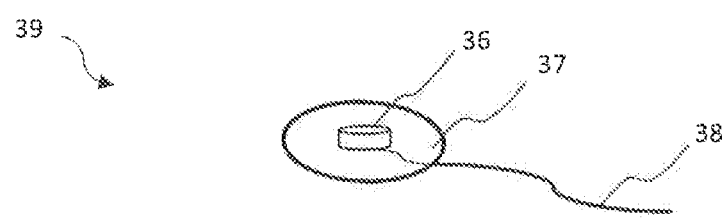
FIG. 9 is an exemplary perspective view of a reference electrode.

Another alternative placement of the electrode array is depicted in FIG. 8 where the at least one of electrode arrays 3 may be applicable to a throat 35 or a face 34 of the patient 25 and the detected movement of the patient may be a movement of at least one face 34 muscle of the patient 25. The movement may be detected by a camera 24 as depicted or the electrical field sensor 23 used as the motion detector. Not shown at least one reference electrode 4 may be applied to the head, chin or throat as well.

An exemplary embodiment of a reference electrode 39 having an electrically conductive element 36 applicable to the skin of the patient. Preferably the reference electrode further comprises an electrically non-conductive material 37 to which the electrically conductive element 36 is coupled. The conductive elements 36 may also be embedded in the electrically non-conductive material. The electrically non-conductive material may have any suitable shape for reference electrode placement to or under the skin of a patient. The electrically non-conductive material 37 may provide a support and/or retaining means for the electrically conductive element 37 of the reference electrode 4. Preferably the reference electrode 4 further has a wire or a cable 38 adapted to electrically connect the conductive elements 36 of the reference electrode with the pulse generator 5 and/or control unit 6.

Figure 10:
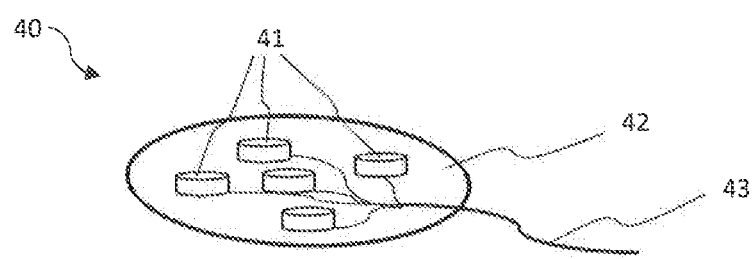
FIG. 10 is an exemplary perspective view of an active electrodes array.

An exemplary embodiment of an electrode array 40 having plurality of active electrodes 2 is depicted in FIG. 10. The plurality of active electrodes may be formed by a plurality of electrically conductive elements 41 electrically isolated from each other. Each of the electrically conductive elements 41 of electrode array 40 may be applicable to the skin of the patient 25 in locations as exemplarily shown in FIGS. 5 to 8 to enable the electrode array placement on the patient 25 body. The shape of electrode array 40 may include of frustoconical, oval, curvy or a flat shape. The electrically conductive elements 41 may be placed in close proximity to each other. The electrically non-conductive material 42 may provide a support and/or retaining means for the electrically conductive elements ensuring that the electrically conductive elements 41 are kept in place and being electrically isolated from each other. Preferably each of the electrically conductive elements 41 comprises a wire or a cable 43 adapted to electrically connect the conductive elements 41 with the pulse generator 5 and/or control unit 6.

Figure 11:
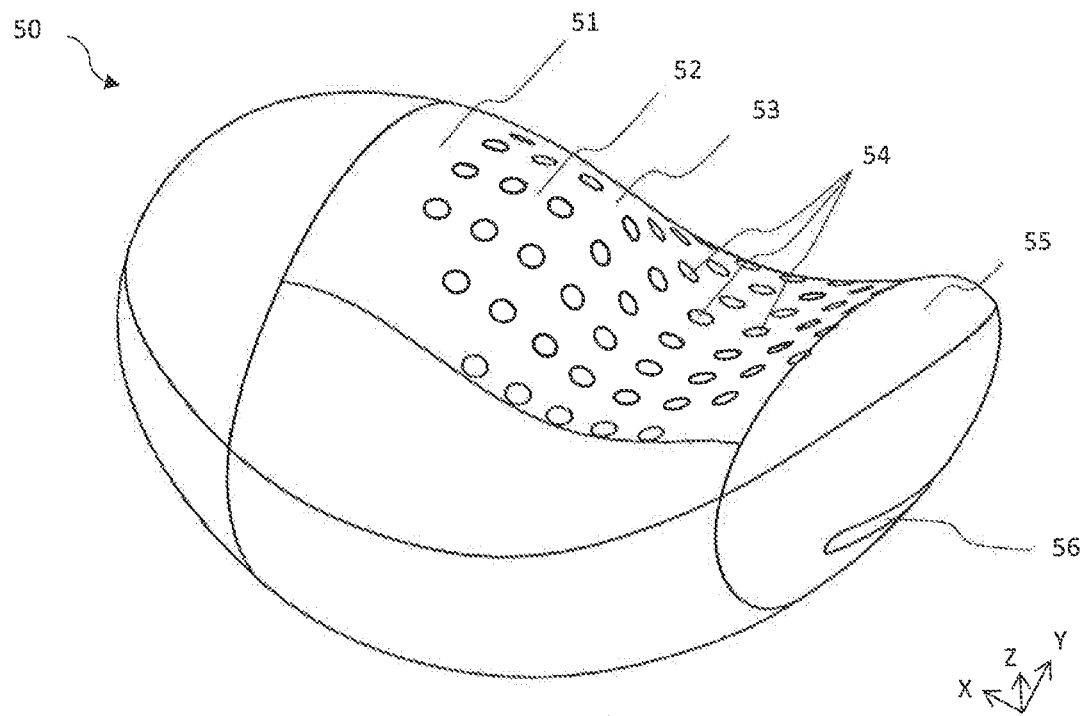
FIG. 11 is an exemplary perspective view of a probe having an electrode array.

The neuromodulation apparatus may further comprise a probe 50. An exemplary embodiment of the probe 50 is depicted in FIG. 11. The probe 50 may have a contact surface 51 which bears an electrode array 53 having plurality of active electrodes 2. Each of the active electrodes 2 has an electrically conductive element 54. The active electrodes 2 may be partially embedded inside the probe 50 having their respective conductive elements 54 protruding outwards from the contact surface 51 of the probe. The contact surface 51 of the probe 50 may comprise a bump 52 which has at least part of the active electrodes of the electrode array 53. The electrode array 53 may extends on the contact surface 51 around the bump. The contact surface 51 has in first direction X a general concave shape from which the bump 52 protrudes. The contact surface may have in second direction Y that is perpendicular to the first direction X a general convex shape. One benefit of having the probe is that the conductive elements of the active electrodes may be advantageously positioned onto the skin of the patient and consequently more effective in delivering electrical pulses to the targeted nerves. The probe may further have at least one recess 56 enabling an attachment of the probe to the patient skin.

Figure 13:
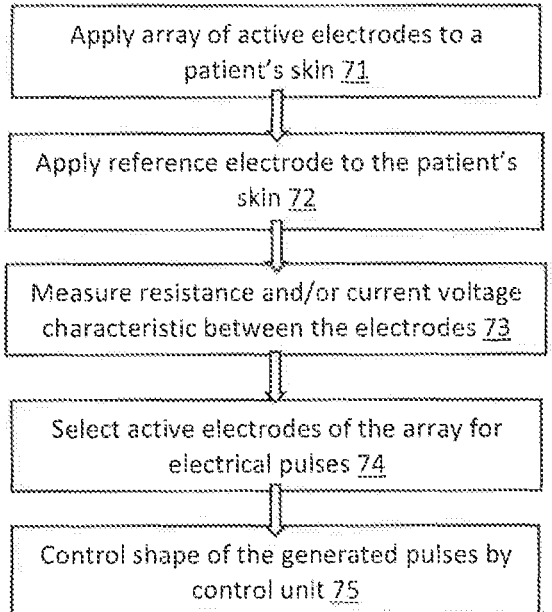
FIG. 13 is a flow diagram depicting an embodiment of a method of using the neuromodulation apparatus.

Referring to FIG. 13, an exemplary flow diagram illustrates an embodiment 70 of a neuromodulation method of using a neuromodulation apparatus. The method 70 may comprise a step 71 of applying at least one electrode array 3 having plurality of active electrodes 2 arranged in it to a skin of a patient. The at least one electrode array 3 may be positioned in the probable location of a target nerve to be modulated or stimulated. The probable location of a target nerve may be a back of the knee or an ankle, a throat or any other suitable location for neuromodulation in the proximity of a target nerve for neuromodulation. The target nerve for neuromodulation may be at least one of sciatic, pudendal, peroneal, cavernous, sacral plexus, a tibial nerve, a lumbosacral plexus, common peroneal, superior gluteal, inferior gluteal, posterior cutaneous femoral, obturator internus, piriformis, quadratus femoris, plantar, vagus or coccygeal nerve.

In step 72 at least one reference electrode 4 may be attached to the skin of the patient. The at least one reference electrode 4 may be attached to an abdomen of the patient 25 or a hip or a waste or an ankle of the patient 25 or elsewhere.

In step 73 a resistance measurement and/or current voltage characteristic may be carried out between each of the active electrode within the at least one electrode array 3 and the at least one reference electrode 4.

In step 74 based upon the measured values may be selected an active electrode or active electrodes of the plurality of active electrodes 2 within the at least one electrode array 3 for receiving an electrical pulse generated by a pulse generator electrically selectively connected to each active electrode of the plurality of active electrodes.

In step 75 electrical pulses may be generated by a pulse generator and their shape may be controlled by the control unit based on the measured values of resistance and/or current voltage characteristic.

The method 70 may further comprise a step of repeatable measurements of the resistance and/or the current voltage characteristic between each of active electrodes within the at least one electrode array 3 and the at least one reference electrode 4. Based on the measurement results the selection may be updated of which of an active electrode or active electrodes within the electrode array is to receive the electrical pulses generated by the pulse generator.

The method 70 may further comprise a step of detecting a response of the patient's body to the at least one pulse generated by the pulse generator and providing feedback on the detected response to the control unit.

One benefit of the method is that based on the measurement results it may be determined which of active electrodes within the electrode array is to receive electrical pulses generated by the pulse generator and the shape of the electrical pulses such as their magnitude 61, pulse width 62, pulse period 63 and/or raising/falling edge. Hence such method may enable to set an optimal shape of the pulses generated by the pulse generator individually for each patient and find an active electrode within the electrode array that is closest to the targeted nerve.

Another benefit of the method may be that the measurement of the resistance or current-voltage characteristic between each of the active electrodes and the reference electrode may provide a verification that the active electrodes and reference electrode is properly attached to the skin of the patient 25. In case an either active of reference electrode is not attached properly to the skin of the patient the resistance measurement between the electrode and another electrode would display that in the measured value.

Another benefit may be that the measurement of the resistance or current-voltage characteristic between each of the active electrode and the reference electrode can be used for a self-check of operation of the neuromodulation apparatus 1. Such self-check may be achieved when plurality of subsequent measurements are taken and their results compared. For that periodical measurements of the resistance or current-voltage characteristic may be taken. Alternatively single non-periodical measurements of the resistance or current-voltage characteristic may be taken and used for self-check during the operation of the neuromodulation apparatus 1. For instance taking initial measurement and then a non-periodical or ad-hoc measurements at discrete intervals. Periodical, non-periodical or ad-hoc measurement of the resistance or current-voltage characteristic may be combined to achieve an automatic self-check functionality of the neuromodulation apparatus 1. Such technical self-check provides during the neuromodulation apparatus use a verification of the neuromodulation apparatus functionality and so enables due to the repeated measurements of the resistance or current-voltage characteristic to ensure safety and an efficiency of the target nerve neuromodulation or stimulation.

Figure 14:
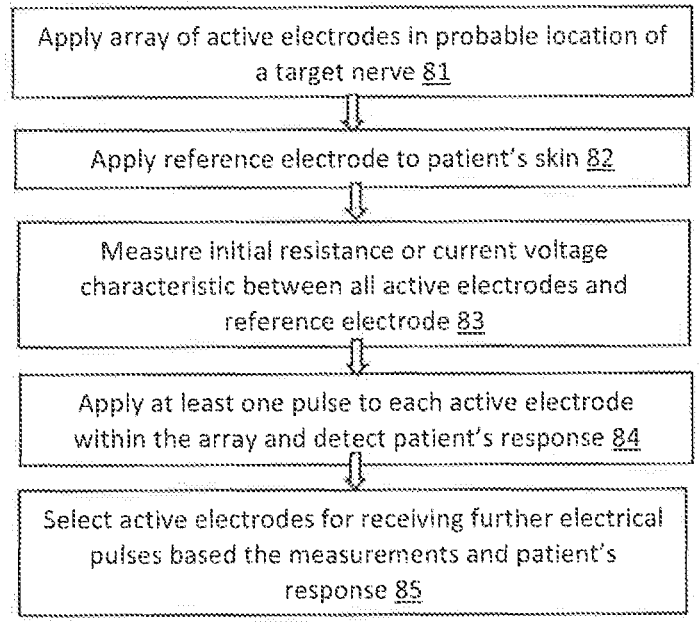
FIG. 14 is a flow diagram depicting an embodiment of a method of determining pulse shape.

In FIG. 14, an exemplary flow diagram illustrates another embodiment 80 of a neuromodulation method. The method 80 may be used in conjunction with, or as part of, the method 70 of FIG. 13. The method 80 may comprise step 81 of applying at least one electrode array 3 having plurality of active electrodes 2 to a skin of a patient in a probable location of a target nerve to be modulated or stimulated. The probable location of a target nerve may be a back of the knee, an ankle, a throat or any other suitable location for neuromodulation in the proximity of a target nerve for neuromodulation. The target nerve for neuromodulation may be at least one of sciatic, pudendal, peroneal, cavernous, sacral plexus, a tibial nerve, a lumbosacral plexus, common peroneal, superior gluteal, inferior gluteal, posterior cutaneous femoral, obturator internus, piriformis, quadratus femoris, vagus, plantar or coccygeal nerve.

In step 82 at least one reference electrode 4 may be attached to or under the skin of the patient 25. The at least one reference electrode 4 may be attached to an abdomen of the patient 25 or a hip or a waste of the patient 25 or elsewhere.

In step 83 an initial measurement of a resistance or current voltage characteristic may be carried out between each of the active electrode within the at least one electrode array 3 and the at least one reference electrode 4.

In step 84 at least one pulse generated by the pulse generator is applied to each individual active electrodes of the plurality of electrodes within the at least one electrode array 3 and a patient's response is detected by a detector for each active electrode of the plurality of electrodes. The at least one pulse may be applied sequentially to each individual active electrode of the plurality of active electrodes 2. One benefit of applying pulse sequentially one by one to each of the active electrode of the plurality electrodes is that the level of patient response may be utilized in an initial calibration of a neuromodulation apparatus to a specific patient.

In step 85 is selected an active electrode or active electrodes for receiving further electrical pulses based on resistance and/or current voltage measurement and/or the patient's response detected by the detector for each individual active electrode of the plurality of electrodes 2 within the at least one electrode array 3.

The method 80 may further comprise a step of repeatable measurements of the resistance and/or the current voltage characteristic between each of active electrodes within the at least one electrode array 3 and the at least one reference electrode 4. Based on the measurement results the selection may be updated of which of an active electrode or active electrodes within the electrode array is to receive the electrical pulses generated by the pulse generator.

The method 80 may further comprise a step of determining current density of electrical pulses flowing through each of selected active electrodes 2. Based on the result of the current density the method may also select further active electrodes neighboring to the each of the selected active electrodes within the same electrodes array to also receive electrical pulses generated by the pulse generator. One benefit may be to prevent an excessive current density of the electrical pulses flowing through each of selected active electrode applied to or under the skin of the patient.

One benefit the method 80 may be that the combination of resistance measurement and/or current voltage characteristic together with detector response enables to locate the active electrode in the most effective position to enable effective modulation of the target nerve.

While various spatial and directional terms, such as top, bottom, lower, mid, lateral, horizontal, vertical, front and the like may be used to describe embodiments of the present disclosure, it is understood that such terms are merely used with respect to the orientations shown in the drawings. The orientations may be inverted, rotated, or otherwise changed, such that an upper portion is a lower portion, and vice versa, horizontal becomes vertical, and the like.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments of the disclosure without departing from their scope. While the dimensions and types of materials described herein are intended to define the parameters of the various embodiments of the disclosure, the embodiments are by no means limiting and are exemplary embodiments. Many other embodiments will be apparent to those of skill in the art upon reviewing the above description. The scope of the various embodiments of the disclosure should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

This written description uses examples to disclose the various embodiments of the disclosure, including the best mode, and also to enable any person skilled in the art to practice the various embodiments of the disclosure, including making and using any devices or systems and performing any incorporated methods. The patentable scope of the various embodiments of the disclosure is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal languages of the claims.

What is claimed is:

1. A neuromodulation apparatus for a medical treatment comprising:
   a plurality of active electrodes electrically isolated from each other and arranged in at least one electrodes array, wherein each active electrode comprises an electrically conductive element configured to be applied to a skin of a patient;

at least one reference electrode configured to be applied to the skin of the patient;

a pulse generator electrically connected to each active electrode of the plurality of active electrodes and configured to selectively transmit electric pulses for the neuromodulation medical treatment to each of the plurality of active electrodes;

a control unit coupled to the electrical pulse generator and adapted to measure a resistance and/or a current-voltage characteristic between each active electrode of the plurality of active electrodes and the at least one reference electrode, wherein based on the measured resistance and/or current-voltage characteristic the control unit is adapted to both control a shape of the electrical pulses and select which an active electrode or active electrodes of the plurality of active electrodes are to receive the electrical pulses for the neuromodulation medical treatment generated by the pulse generator, wherein the control unit is further configured to determine a current density of electrical pulses for the neuromodulation medical treatment flowing through each of selected active electrodes during the neuromodulation medical treatment and based on the result selectively employ active electrodes neighboring to the each of the selected active electrodes within the same electrodes array to also receive electrical pulses for the neuromodulation medical treatment generated by the pulse generator.

2. The apparatus according to claim 1, wherein the control unit is configured to repeatably measure the resistance and/or the current-voltage characteristic between each active electrode of the plurality of active electrodes and the at least one reference electrode.

3. The apparatus according to claim 2, wherein based on the repeatable measurement the control unit is further configured to update the selection of which of an active electrode or active electrodes of the plurality of active electrodes are to receive the electrical pulses for the neuromodulation medical treatment generated by the pulse generator.

4. The apparatus according to claim 1, further comprising at least one detector configured to detect a response of the patient to at least one electrical pulse for the neuromodulation medical treatment generated by the pulse generator, wherein the detector is further adapted to provide feedback on the detected response to the control unit.

5. The apparatus according to claim 4, wherein the at least one detector is at least one motion detector configured to detect a movement of the patient and adapted to provide feedback on the movement to the control unit, wherein the movement of the patient body is in response to the at least one pulse of the pulse generator.

6. The apparatus according to claim 5, wherein the at least one motion detector includes at least one of an accelerometer, an electrical field sensor or a camera.

7. The apparatus according to claim 4, wherein the control unit is further adapted to individually select each of the active electrodes of the plurality of electrodes for a reception of at least one electrical pulse for the neuromodulation medical treatment generated by the pulse generator and the control unit is further adapted to receive a patient's response detected by the detector to the at least one electrical pulse for the neuromodulation medical treatment generated by the pulse generator for each of the individually selected active electrodes of the plurality of electrodes.

8. The apparatus according to claim 7, wherein the control unit is adapted to both control a shape of the electrical pulses for the neuromodulation medical treatment and select which active electrodes of the plurality of active electrodes are to receive the electrical pulses for the neuromodulation medical treatment generated by the pulse generator based on the measured resistance and/or current-voltage characteristic and the detected response by the at least one detector.

9. The apparatus according to claim 1, wherein the control unit is configured to control a slope of rising edge of the electric pulses and/or a magnitude of the electric pulses for the neuromodulation medical treatment.

10. The apparatus according to claim 1, wherein the control unit is further configured to control a pulse period and/or a pulse width of the electric pulses for the neuromodulation medical treatment.

11. The apparatus according to claim 1, further including a probe having a contact surface which bears the electrode array, the contact surface comprising a bump which has at least part of the active electrodes of the electrode array.

12. The apparatus according to claim 11, wherein the electrode array extends on the contact surface around the bump.

13. The apparatus according to claim 11, wherein the contact surface has in first direction a general concave shape from which the bump protrudes, wherein the contact surface has in second direction that is perpendicular to the first direction a general convex shape.

14. A method of using a neuromodulation apparatus for a neuromodulation medical treatment, comprising:

applying a plurality of active electrodes arranged in at least one electrodes array to a skin of a patient in an expected location of a target nerve to be stimulated or modulated, wherein the active electrodes are electrically isolated from each other;

applying at least one reference electrode to the skin of the patient;

measuring by a control unit a resistance and/or a current-voltage characteristic between each active electrode of the plurality of active electrodes and the at least one reference electrode;

selecting based on the measured values by the control unit an active electrode or active electrodes of the plurality of active electrodes for receiving at least one electrical pulse for the neuromodulation medical treatment generated by a pulse generator electrically selectively connected to each active electrode of the plurality of active electrodes;

controlling by the control unit a shape of the electrical pulses for the neuromodulation medical treatment generated by the pulse generator based on the measured value; and determining a current density of electrical pulses for the neuromodulation medical treatment flowing through each of selected active electrodes during the neuromodulation medical treatment and based on the result selectively employing active electrodes neighboring to the each of the selected active electrodes within the same electrodes array to also receive electrical pulses for the neuromodulation medical treatment generated by the pulse generator.

15. The method of claim 14, wherein the target nerve is at least one of sciatic, pudendal, peroneal, cavernous, sacral plexus, vagus or a tibial nerve.

16. The method of claim 14, wherein the method comprises repeatably measuring the resistance and/or the current—voltage characteristic between each of active electrodes arranged within each of the at least one electrodes array and each of the at least one reference electrode and updating the measured values with the new measurements for each of the at least one electrode array.

17. The method of claim 14, wherein the method comprises detecting a response of the patient's body to the at least one electrical pulse for the neuromodulation medical treatment generated by the pulse generator and providing feedback on the detected response to the control unit.

18. The method of claim 14, wherein the method comprises applying at least one electrical pulse for the neuromodulation medical treatment generated by the pulse generator to each individual active electrodes of the plurality of electrodes and receiving a patient's response detected by the detector for each active electrode of the plurality of electrodes.

19. The method of claim 14, wherein the selecting the active electrodes for receiving the at least one electrical pulse for the neuromodulation medical treatment generated by a pulse generator is also based on the patient's response detected by the detector for each individual active electrode of the plurality of electrodes.

\* \* \* \* \*